(12) United States Patent
Babu et al.

(10) Patent No.: US 8,895,729 B2
(45) Date of Patent: Nov. 25, 2014

(54) PROCESS FOR MAKING THIENOPYRIMIDINE COMPOUNDS

(71) Applicant: Genentech, Inc., South San Francisco, CA (US)

(72) Inventors: Srinivasan Babu, San Diego, CA (US); Zhigang Cheng, San Ramon, CA (US); Francis Gosselin, San Mateo, CA (US); Pirmin Hidber, Basel (CH); Ursula Hoffmann, Basel (CH); Theresa Humphries, San Francisco, CA (US); Reinhard Reents, Basel (CH); Qingping Tian, Palo Alto, CA (US); Herbert Yajima, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 14/049,477

(22) Filed: Oct. 9, 2013

(65) Prior Publication Data

US 2014/0100366 A1    Apr. 10, 2014

Related U.S. Application Data

(60) Provisional application No. 61/711,900, filed on Oct. 10, 2012.

(51) Int. Cl.
*C07D 495/04* (2006.01)
*C07D 295/185* (2006.01)
*C07D 491/00* (2006.01)

(52) U.S. Cl.
CPC .......... *C07D 495/04* (2013.01); *C07D 295/185* (2013.01)
USPC ............................ 544/117; 544/386; 544/278

(58) Field of Classification Search
USPC ................................. 544/117, 386
See application file for complete search history.

(56) References Cited

U.S. PATENT DOCUMENTS

| 7,888,352 | B2 | 2/2011 | Bayliss et al. |
| 8,383,620 | B2 | 2/2013 | Bayliss et al. |
| 2008/0076758 | A1 | 3/2008 | Folkes et al. |
| 2009/0098135 | A1 | 4/2009 | Belvin et al. |
| 2010/0292468 | A1 | 11/2010 | Babu et al. |
| 2012/0308562 | A1 | 12/2012 | Derynck et al. |

FOREIGN PATENT DOCUMENTS

| WO | 2006/046040 | A1 | 5/2006 |
| WO | 2008/070740 | A1 | 6/2008 |
| WO | 2008/073785 | A2 | 6/2008 |
| WO | 2010/105008 | A2 | 9/2010 |

OTHER PUBLICATIONS

Folkes et al., "The identification of 2-(1H-indazol-4-yl)-6-(4-methanesulfonyl-piperazin-1-ylmethyl)-4-morpholin-4-yl-thieno[3,2-d]pyrimidin e (GDC-0941) as a potent, selective, orally bioavailable inhibitor of class I PI3 kinase for the treatment of cancer" J Med Chem 51(18):5522-5532 ( 2008).

Heffron et al., "Identification of GNE-477, a potent and efficacious dual PI3K/mTOR inhibitor" Bioorg Med Chem Lett. 20:2408-11 ( 2010).

Heffron et al., "Rational design of phosphoinositide 3-kinase α inhibitors that exhibit selectivity over the phosphoinositide 3-kinase β isoform" J Med Chem. 54:7815-33 ( 2011).

Heffron et al., "The design and identification of brain penetrant inhibitors of phosphoinositide 3-kinase α" J Med Chem. 55:8007-20 ( 2012).

PCT ISR for PCT/EP2013/070994, Apr. 17, 2014.

Staben et al., "Structure-based design of thienobenzoxepin inhibitors of PI3-kinase" Bioorg Med Chem Lett. 21:4054-8 ( 2011).

Sutherlin et al., "Discovery of (Thienopyrimidin-2-yl)aminopyrimidines as Potent, Selective, and Orally Available Pan-PI3-Kinase and Dual Pan-PI3-Kinase/mTOR Inhibitors for the Treatment of Cancer" J Med Chem 53(3):1086-1097 ( 2010).

Sutherlin et al., "Discovery of a potent, selective, and orally available class I phosphatidylinositol 3-kinase (PI3K)/mammalian target of rapamycin (mTOR) kinase inhibitor (GDC-0980) for the treatment of cancer" J Med Chem. 54(21):7579-87 ( 2011).

Wallin et al., "GDC-0980 is a novel class I PI3K/mTOR kinase inhibitor with robust activity in cancer models driven by the PI3K pathway" Mol Cancer Ther. 10(12):2426-36 ( 2011).

*Primary Examiner* — Jeffrey H Murray
*Assistant Examiner* — Oluwafemi Masha
(74) *Attorney, Agent, or Firm* — Alex Andrus; Genentech, Inc.

(57) ABSTRACT

Process methods for making the dual mTOR/PI3K inhibitor GDC-0980, named as (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one, having the structure:

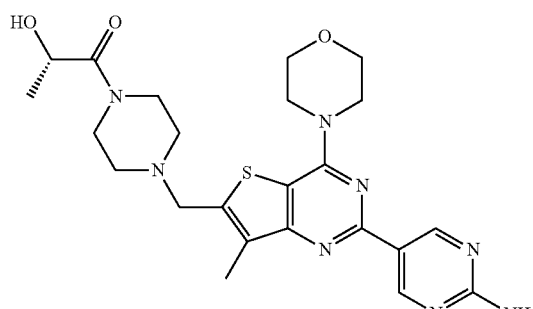

and stereoisomers, geometric isomers, tautomers, and pharmaceutically acceptable salts thereof.

15 Claims, No Drawings

PROCESS FOR MAKING THIENOPYRIMIDINE COMPOUNDS

CROSS REFERENCE TO RELATED APPLICATIONS

This non-provisional application filed under 37 CFR §1.53 (b), claims the benefit under 35 USC §119(e) of U.S. Provisional Application Ser. No. 61/711,900 filed on 10 Oct. 2012, which is incorporated by reference in entirety.

FIELD OF THE INVENTION

The invention relates to methods of making a PI3K inhibitor compound GDC-0980.

BACKGROUND OF THE INVENTION

Phosphoinositide 3-kinases (PI3K) are lipid kinases that phosphorylate lipids at the 3-hydroxyl residue of an inositol ring (Whitman et al (1988) Nature, 332:664). The 3-phosphorylated phospholipids (PIP3s) generated by PI3-kinases act as second messengers recruiting kinases with lipid binding domains (including plekstrin homology (PH) regions), such as Akt and phosphoinositide-dependent kinase-1 (PDK1). Binding of Akt to membrane PIP3s causes the translocation of Akt to the plasma membrane, bringing Akt into contact with PDK1, which is responsible for activating Akt. The tumor-suppressor phosphatase, PTEN, dephosphorylates PIP3 and therefore acts as a negative regulator of Akt activation. The PI3-kinases Akt and PDK1 are important in the regulation of many cellular processes including cell cycle regulation, proliferation, survival, apoptosis and motility and are significant components of the molecular mechanisms of diseases such as cancer, diabetes and immune inflammation (Vivanco et al (2002) Nature Rev. Cancer 2:489; Phillips et al (1998) Cancer 83:41).

The main PI3-kinase isoform in cancer is the Class I PI3-kinase, p110 α (alpha) (U.S. Pat. No. 5,824,492; U.S. Pat. No. 5,846,824; U.S. Pat. No. 6,274,327). Other isoforms are implicated in cardiovascular and immune-inflammatory disease (Workman P (2004) Biochem Soc Trans 32:393-396; Patel et al (2004) Proceedings of the American Association of Cancer Research (Abstract LB-247) 95th Annual Meeting, March 27-31, Orlando, Fla., USA; Ahmadi K and Waterfield M D (2004) Encyclopedia of Biological Chemistry (Lennarz W J, Lane M D eds) Elsevier/Academic Press). The PI3 kinase/Akt/PTEN pathway is an attractive target for cancer drug development since such modulating or inhibitory agents would be expected to inhibit proliferation, reverse the repression of apoptosis and surmount resistance to cytotoxic agents in cancer cells (Folkes et al (2008) J. Med. Chem. 51:5522-5532; Yaguchi et al (2006) Jour. of the Nat. Cancer Inst. 98(8):545-556). The PI3K-PTEN-AKT signaling pathway is deregulated in a wide variety of cancers (Samuels Y, Wang Z, Bardellil A et al. High frequency of mutations of the PIK3CA gene in human cancers. (2004) Science; 304 (5670):554; Carpten J, Faber A L, Horn C. "A transforming mutation in the pleckstrin homology domain of AKT1 in cancer" (2007) Nature; 448:439-444).

GDC-0980 (Genentech, Inc., Roche, RG-7422) demonstrates broad activity in preclinical xenograft cancer models; breast, ovarian, lung, and prostate, and is being developed for the potential oral treatment of cancer including solid tumors and non-Hodgkin's lymphoma (Wagner A J; Burris III HA; de Bono J S et al AACR-NCI-EORTC International Congress (2009), 21st:November 17 (Abs B137) "Pharmacokinetics and Pharmacodynamic biomarkers for the dual PI3K/mTOR inhibitor GDC-0980: initial phase I evaluation"; U.S. Pat. No. 7,888,352; US 2009/0098135; US 2010/0233164). In March 2009, a phase I trial in patients with solid tumors or NHL was initiated; in April 2009, a second phase I trial began; these trials were ongoing in April 2010. In December 2010, a phase Ib combination trial in metastatic breast cancer was initiated. In July 2010, a phase II trial in metastatic breast cancer was planned for the first half of 2011; patients would receive GDC-0980 combined with hormonal therapy. Clinical results to date suggest that GDC-0980 may benefit patients with solid tumors or hematological malignancies. (Sutherlin D P, Belvin M, Bao L et al, American Association for Cancer Research Annual Meeting, (2011) 102nd:April 04 (Abs 2787)).

GDC-0980 is a potent, selective, oral inhibitor of Class I PI3K and mTOR kinase with the following in vitro biochemical IC50s against Class I isoforms of PI3K: p110α (alpha) 4.8 nM; p110β (beta) 26.8 nM; p110 (gamma) 13.8 nM; p110d (delta) 6.7 nM; mTOR Ki 17.3 nM. GDC-0980 was selective for PI3K versus a large panel of kinases (>145), including other members of the phosphatidylinositol kinase family. In PC3 and MCF7-neo/HER2 cell lines, the compound demonstrated IC50 values of 307 and 320 nM, respectively. GDC-0980 was stable in human microsomes and hepatocytes, exhibited low activity against hERG IC50>100 μM (microM) and did not elicit significant responses in a receptor screening assay (n=68; GDC-0980=10 microM). Moderate-to-high clearance was observed in rodents (60 ml/min/kg) and dogs (12 ml/min/kg). The terminal half-life of the compound was 6 to 18 h, with dose-proportional increases in AUC and Cmax values following a single oral dose. GDC-0980 (25 to 150 mg/kg qd po) was efficacious across multiple xenograft models, including mouse PC3 PTEN-prostate and MCF7.1 E545K breast xenograft models. In a MDA-MB-361.1 breast cancer xenograft model, GDC-0980 produced significant growth inhibition at a minimum dose of 1.0 mg/kg QD.

SUMMARY OF THE INVENTION

The invention relates to methods of making the dual mTOR/PI3K inhibitor GDC-0980, named as (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one, having the structure:

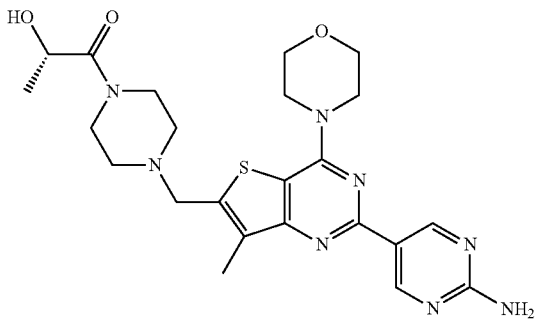

and stereoisomers, geometric isomers, tautomers, and pharmaceutically acceptable salts thereof.

Another aspect of the invention is methods of making intermediate, 2-aminopyrimidin-5-ylboronic acid III, useful for preparing GDC-0980, and having the structure:

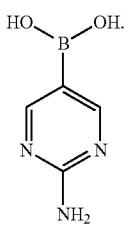

Another aspect of the invention is the novel intermediate, the oxalate salt (S)-2-hydroxy-1-(piperazin-1-yl)propan-1-one V, useful for preparing GDC-0980, and having the structure:

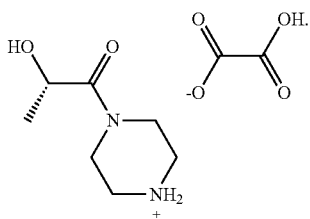

DEFINITIONS

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, glycolic acid, malonic acid, oxalic acid, pyruvic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

PREPARATION OF GDC-0980

The present invention includes processes, methods, reagents, and intermediates for the synthesis of GDC-0980, a small molecule inhibitor of PI3K and mTOR, (CAS Reg. No. 1032754-93-0), which has the structure:

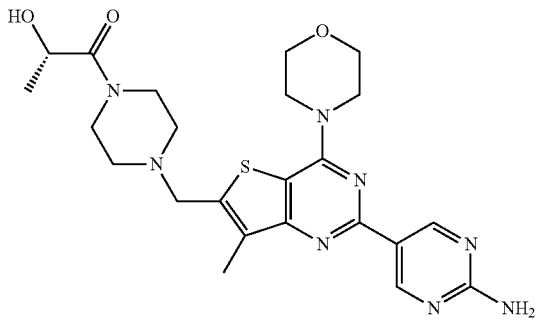 [SMILES: Cc1c(CN2CCN(C(=O)[C@H](C)O)CC2)sc2c(N3CCOCC3)nc(-c3cnc(N)nc3)nc12]

and may be named: (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one (U.S. Pat. No. 7,888,352; US 2009/0098135; US 2010/0233164). As used herein, GDC-0980 includes all stereoisomers, geometric isomers, tautomers, and pharmaceutically acceptable salts thereof.

The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. In addition, the present invention embraces all geometric and positional isomers. In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the invention may exist in unsolvated as well as solvated forms with pharmaceutically acceptable solvents such as water, ethanol, and the like, and it is intended that the invention embrace both solvated and unsolvated forms.

The compounds of the invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The compounds of the invention also include isotopically-labeled compounds which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^{2}$H, $^{3}$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Certain isotopically-labeled compounds of the present invention (e.g., those labeled with $^{3}$H and $^{14}$C) are useful in compound and/or substrate tissue distribution assays. Tritiated ($^{3}$H) and carbon-14 ($^{14}$C) isotopes are useful for their ease of preparation and detectability. Further, substitution with heavier isotopes such as deuterium (i.e., $^{2}$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C and $^{18}$F are useful for positron emission tomography (PET) studies to examine substrate receptor occupancy. Isotopically labeled compounds of the present invention can generally be prepared by following procedures analogous to those disclosed in the Examples herein below, by substituting an isotopically labeled reagent for a non-isotopically labeled reagent.

Starting materials and reagents for the preparation of GDC-0980 are generally available from commercial sources such as Sigma-Aldrich Chemical (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements (also available via the Beilstein online database).

The following Schemes 1-8 illustrate the chemical reactions, processes, methodology for the synthesis of GDC-0980, Formula I, and certain intermediates and reagents. It is understood that other reagents, solvents, and reaction conditions than those illustrated in Schemes 1-8 may be employed to achieve the same transformations.

Scheme 1:

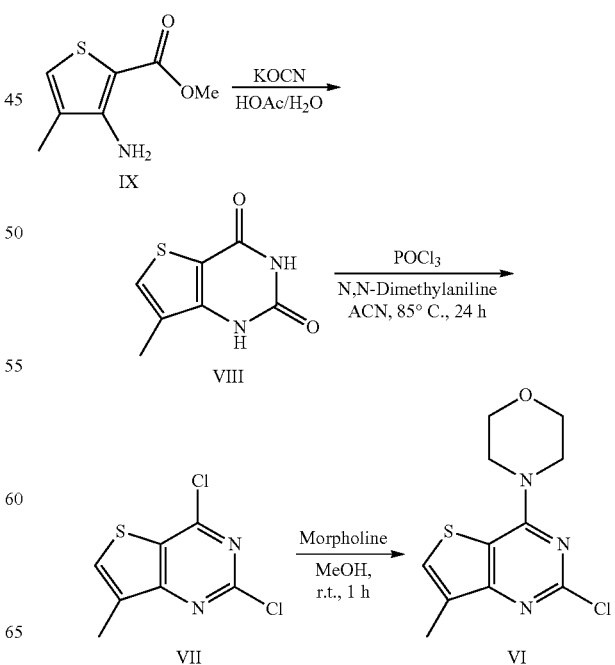

Scheme 1 shows the synthesis of intermediate 4-(2-chloro-7-methylthieno[3,2-d]pyrimidin-4-yl)morpholino VI from methyl 3-amino-4-methylthiophene-2-carboxylate IX. Cyclization of IX with potassium cyanate in acetic acid and water gave 7-methylthieno[3,2-d]pyrimidine-2,4(1H,3H)-dione VIII (Example 1). Chlorination of VIII with phosphorus oxychloride and N,N-dimethylaniline in acetonitrile (ACN) gave 2,4-dichloro-7-methylthieno[3,2-d]pyrimidine VII (Example 2). Substitution of the 4-chloro group of VII with morpholine in methanol gave VI (Example 3).

Scheme 2:

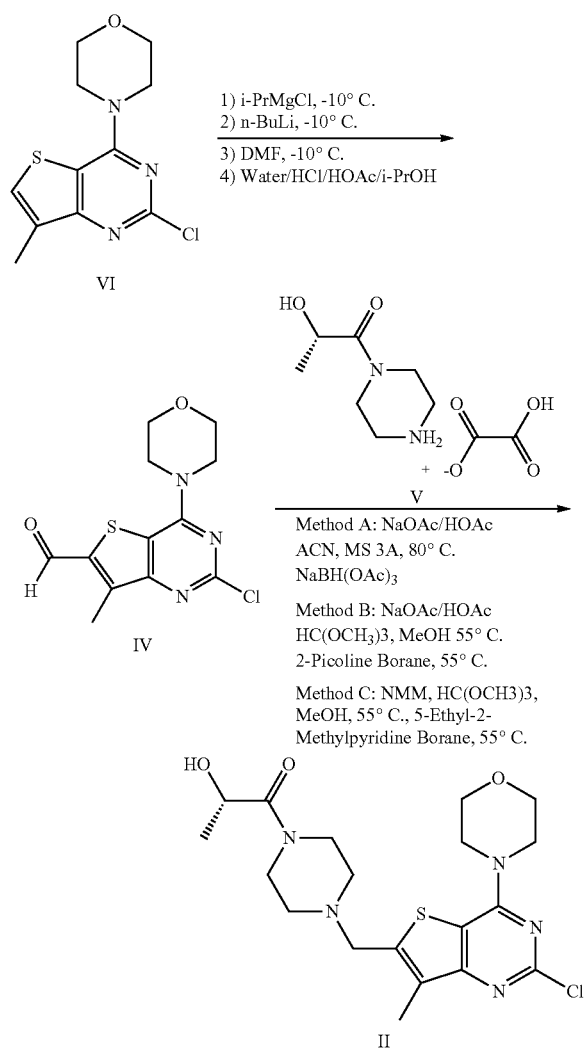

Scheme 2 shows the synthesis of intermediate (S)-1-(4-((2-chloro-7-methyl-4-morpholinothieno[3,2-d]pyrimidin-6-yl)methyl)piperazin-1-yl)-2-hydroxypropan-1-one II from 4-(2-chloro-7-methylthieno[3,2-d]pyrimidin-4-yl)morpholino VI. Treatment of VI with isopropylmagnesium chloride Grignard reagent followed by n-butyllithium at −10° C. was followed by addition of dimethylformamide and quenching with aqueous acid gave formylated intermediate 2-chloro-7-methyl-4-morpholinothieno[3,2-d]pyrimidine-6-carbaldehyde IV (Example 4). Reductive amination of IV was effected by mixing IV with the oxalate salt of (S)-2-hydroxy-1-(piperazin-1-yl)propan-1-one V followed by a reducing agent, such as sodium triacetoxyborohydride (Method A), 2-picoline borane (Method B) or 5-Ethyl-2-methylpyridine borane to give II which was crystallized in toluene/heptane (Example 5) or Me-THF/heptane.

Scheme 3:

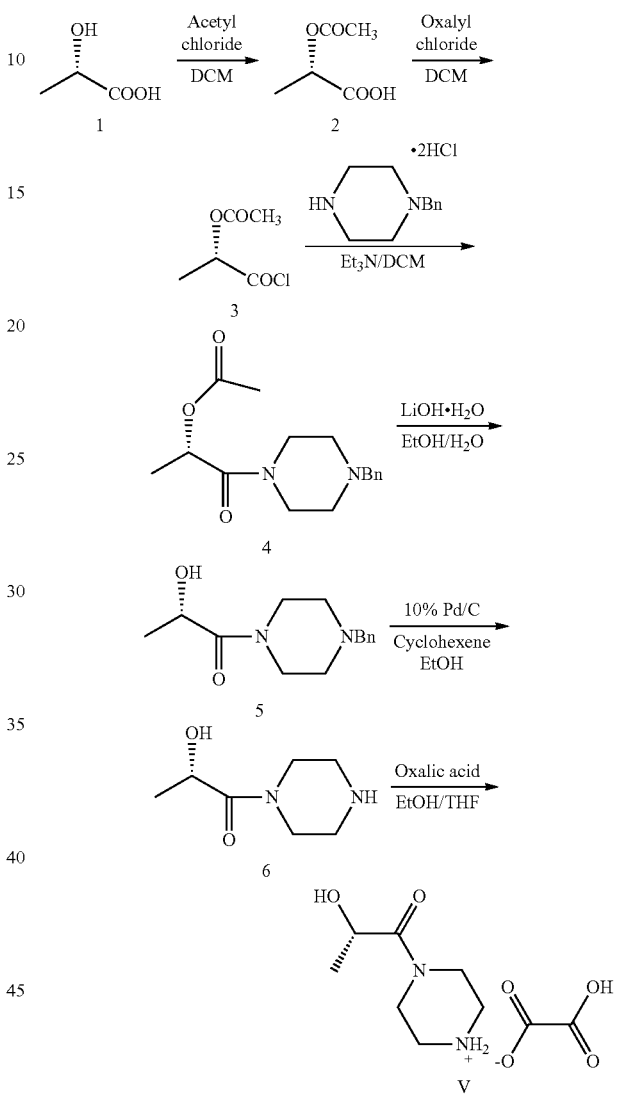

Scheme 3 shows the synthesis of intermediate, oxalate salt of (S)-2-hydroxy-1-(piperazin-1-yl)propan-1-one V from (S)-2-hydroxypropanoic acid (L-lactic acid) 1. Acetylation of 1 gave (S)-2-acetoxypropanoic acid 2, followed by treatment with a chlorinating reagent, such as oxalyl chloride, to give acid chloride, (S)-1-chloro-1-oxopropan-2-yl acetate 3 (Example 6). Reaction of 3 with the dihydrochloride salt of 1-benzylpiperazine in dichloromethane in the presence of triethylamine gave (S)-1-(4-benzylpiperazin-1-yl)-1-oxopropan-2-yl acetate 4 (Example 7). Hydrolysis of the acetate of 4 with lithium hydroxide gave (S)-1-(4-benzylpiperazin-1-yl)-2-hydroxypropan-1-one 5 (Example 8), followed by hydrogenation to remove the N-benzyl group to give (S)-2-hydroxy-1-(piperazin-1-yl)propan-1-one 6 (Example 9). The oxalate salt was formed from 6 with oxalic acid in ethanol and tetrahydrofuran to give V (Example 9).

Scheme 4:

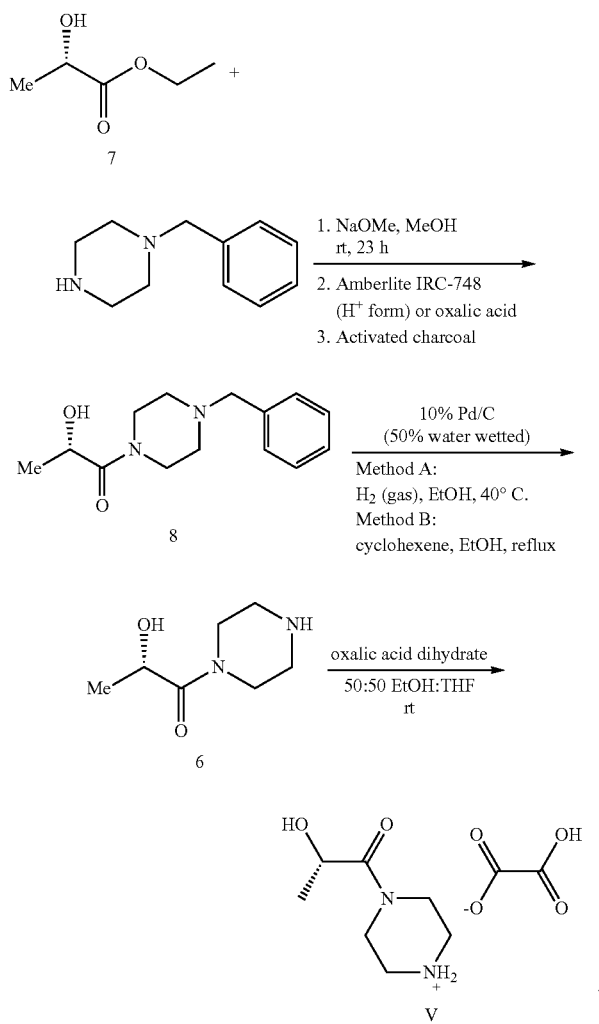

Scheme 5:

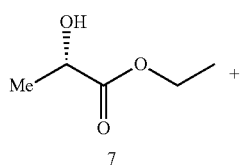

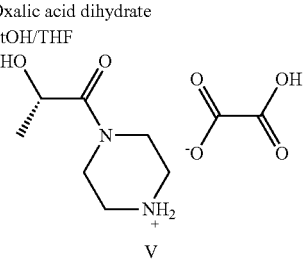

Scheme 5 shows an alternative, one-step synthesis of intermediate oxalate salt of (S)-2-hydroxy-1-(piperazin-1-yl)propan-1-one V from (S)-ethyl 2-hydroxypropanoate 7. Unprotected 7 and piperazine react to form amide V with sodium methoxide in methanol, followed by oxalic acid or AMBERLITE® resin IRC-748 treatment to remove impurities, and formation of the oxalate salt (Example 12).

Scheme 6:

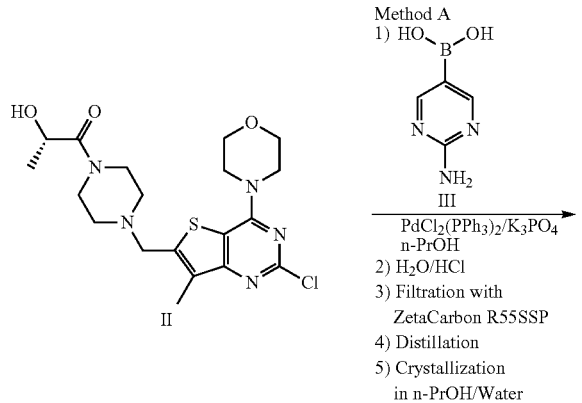

Method B
1) 2-Aminopyrimidin-5-ylboronic acid III, PdCl$_2$(PPh$_3$)$_2$/KHPO$_4$, n-PrOH, water
2) Fitration with ZetaCarbon R55SP
3) Distillation
5) Crystallization in n-PrOH/Water Scheme 4 shows the synthesis of intermediate (S)-2-hydroxy-1-(piperazin-1-yl)propan-1-one V from (S)-ethyl 2-hydroxypropanoate 7. 1-Benzylpiperazine and 7 were reacted in sodium methoxide and methanol to give (S)-1-(4-benzylpiperazin-1-yl)-2-hydroxypropan-1-one 8, isolated from AMBERLITE® IRC-748 resin or oxalic acid, followed by the activated charcoal treatment (Example 10). Reductive cleavage removal of the benzyl group from 8 was effected by palladium catalysis with either hydrogen gas (Method A) or cyclohexene (Method B) to give intermediate (S)-2-hydroxy-1-(piperazin-1-yl)propan-1-one 6 (Example 11). The oxalate salt was formed from 6 with oxalic acid in ethanol and tetrahydrofuran to give V (Example 11).

Scheme 6 shows the synthesis of (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one, GDC-0980, Formula I from intermediate (S)-1-(4-((2- chloro-7-methyl-4-morpholinothieno[3,2-d]pyrimidin-6-yl) methyl)piperazin-1-yl)-2-hydroxypropan-1-one II. Suzuki-Miyaura coupling of II and 2-aminopyrimidin-5-ylboronic acid III with palladium catalysis gives crude I (Example 13). Water was added to quench the reaction mixture followed by recirculating filtration through activated carbon to remove palladium. Volatiles were removed under vacuum and I was crystallized from n-propanol and water to give the free base, GDC-0980, Formula I. In method B the reaction is performed using KHPO4 as a base in n-propanol/water as solvent.

A variety of palladium catalysts can be used during the Suzuki-Miyaura coupling step to form compound I. Suzuki-Miyaura coupling is a palladium mediated cross coupling reaction of an arylhalide, such as II, with a boronic acid such as III. Low valent, Pd(II) and Pd(0) catalysts may be used to prepare I, including $PdCl_2(PPh_3)_2$, $Pd(t-Bu)_3$, $PdCl_2$ dppf $CH_2Cl_2$, $Pd(PPh_3)_4$, $Pd(OAc)/PPh_3$, $Cl_2Pd[(Pet_3)]_2$, $Pd(DIPHOS)_2$, $Cl_2Pd(Bipy)$, $[PdCl(Ph_2PCH_2PPh_2)]_2$, $Cl_2Pd[P(o-tol)_3]_2$, $Pd_2(dba)_3/P(o-tol)_3$, $Pd_2(dba)/P(furyl)_3$, $Cl_2Pd[P(furyl)_3]_2$, $Cl_2Pd(PMePh_2)_2$, $Cl_2Pd[P(4-F-Ph)_3]_2$, $Cl_2Pd[P(C_6F_6)_3]_2$, $Cl_2Pd[P(2-COOH-Ph)(Ph)_2]_2$, $Cl_2Pd[P(4-COOH-Ph)(Ph)_2]_2$, and encapsulated catalysts Pd EnCat™ 30, Pd EnCat™ TPP30, and Pd(II)EnCat™ BINAP30 (US 2004/0254066).

A variety of solid adsorbent palladium scavengers can be used to remove palladium after the Suzuki-Miyaura coupling step to form compound I. Exemplary embodiments of palladium scavengers include FLORISIL®, SILIABOND®Thiol, and SILIABOND® Thiourea. Other palladium scavengers include silica gel, controlled-pore glass (TosoHaas), and derivatized low crosslinked polystyrene QUADRAPURE™ AEA, QUADRAPURE™ IMDAZ, QUADRAPURE™ MPA, QUADRAPURE™ TU (Reaxa Ltd., Sigma-Aldrich Chemical Co.).

The reaction of arylhalide, such as II, and a boronic acid such as III, to form compound I can also be conducted under Buchwald palladium catalysis conditions with the Buchwald pre-catalyst palladacycle and ligand reagents in Table 1 and as described in: Biscoe et al (2008) J. Am. Chem. Soc. 130: 6686-6687; Kinzel et al (2010) J. Am. Chem. Soc. 132: 14073-14075; Molander et al (2012) J. Am. Chem. Soc. 134: 11667-11673; Walker et al (2004) Angew. Chem. Int. Ed. 43:1871; Billingsley et al (2007) Angew. Chem. Int. Ed. 46:5359-5363; U.S. Pat. Nos. 6,946,560; 7,026,498; 7,247,731; 7,560,582; 6,307,087; 6,395,916; 7,223,879; 7,858,784, which are incorporated by reference. Such reagents are commercially available (Johnson Matthey Inc., Wayne, Pa.; Sigma Aldrich Fine Chemical, St. Louis, Mo.; Strem Chemicals, Inc., Newburyport, Mass.).

TABLE 1

| Buchwald Catalysts and Ligands | Name | CAS Reg. No. |
|---|---|---|
| 2-Dicyclohexylphosphino-2'-(N,N-dimethylamino)biphenyl | DavePhos | 213697-53-1 |
| 2-Dicyclohexylphosphino-2',4',6'-triisopropylbiphenyl | XPhos | 564483-18-7 |
| 2-Dicyclohexylphosphino-2',6'-dimethoxybiphenyl | SPhos | 657408-07-6 |
| 2-Di-tert-butylphosphino-2',4',6'-triisopropylbiphenyl | tBuXPhos | 564483-19-8 |
| (2-Biphenyl)dicyclohexylphosphine | CyJohnPhos | 247940-06-3 |
| (2-Biphenyl)di-tert-butylphosphine | JohnPhos | 224311-51-7 |
| Sodium 2'-dicyclohexylphosphino-2,6 dimethoxy-1,1'-biphenyl-3-sulfonate hydrate | SPhos [water soluble] | 1049726-96-6 |
| 2-Di-tert-butylphosphino-3,4,5,6-tetramethyl-2',4',6'-triisopropyl-1,1'-biphenyl | Tetramethyl tBuXPhos | 857356-94-6 |
| 2-Dicyclohexylphosphino-2',6'-diisopropoxybiphenyl | RuPhos | 787618-22-8 |
| 2'-(Diphenylphosphino)-N,N'-dimethyl-(1,1'-biphenyl)-2-amine, 2-Diphenylphosphino-2'-(N,N-dimethylamino)biphenyl | PhDave-Phos | 240417-00-9 |
| 2'-(Di-tert-butylphosphino)-N,N-dimethylbiphenyl-2-amine | t-BuDavePhos | 224311-49-3 |
| 2-Dicyclohexylphosphino-2'-methylbiphenyl, 2-Methyl-2'-dicyclohexylphosphinobiphenyl | MePhos | 251320-86-2 |
| 2-Di-tert-butylphosphino-2'-methylbiphenyl | tBuMePhos | 255837-19-5 |
| Au(MeCN)SbF$_6$ | JohnPhos | 866641-66-9 |
| (2-Biphenyl)di-tert-butylphosphine gold(I) chloride, 2-(Di-tert-butylphosphino)biphenyl gold(I) chloride | JohnPhos AuCl | 854045-93-5 |
| 2-Dicyclohexylphosphino-2',4',6'-triisopropylbiphenyl gold(I) chloride | XPhos AuCl | 854045-94-6 |
| 2-Dicyclohexylphosphino-2',4',6'-triisopropylbiphenyl gold(I) bis(trifluoromethanesulfonyl)imide | XPhos AuNTf$_2$ | 934506-10-2 |
| 2-(Dicyclohexylphosphino)3,6-dimethoxy-2',4',6'-triisopropyl-1,1'-biphenyl RuPhos Pd G1 Methyl-t-Butyl Ether Adduct | BrettPhos | 1070663-78-3 |
| Chloro(2-dicyclohexylphosphino-2',4',6'-triisopropyl-1,1'-biphenyl)[2-(2-aminoethyl)phenyl)]palladium(II) | XPhos Palladacycle | 1028206-56-5 |
| Chloro(2-dicyclohexylphosphino-2',6'-dimethoxy-1,1'-biphenyl)[2-(2-aminoethylphenyl)]palladium(II)-methyl-t-butyl ether adduct | SPhos Palladacycle | |
| t-BuXPhos palladium(II) phenethylamine chloride | tBuXPhos Pd G1 | 1142811-12-8 |
| 2-{Bis[3,5-bis(trifluoromethyl)phenyl]phosphino}-3,6-dimethoxy-2',4',6'-triisopropyl-1,1'-biphenyl | JackiePhos | 1160861-60-8 |
| 2-(Di-tert-butylphosphino)-2',4',6'-triisopropyl-3,6-dimethoxy-1,1'-biphenyl | tBuBrettPhos | 1160861-53-9 |
| Dicyclohexyl(2',4',6'-trimethoxy[1,1'-biphenyl]-2-yl)phosphine BrettPhos Pd G1 Methyl-t-Butyl Ether Adduct | | 1000171-05-0 |

TABLE 1-continued

| Buchwald Catalysts and Ligands | Name | CAS Reg. No. |
|---|---|---|
| Chloro(2-dicyclohexylphosphino-2',4',6'-triisopropyl-1,1'-biphenyl)[2-(2'-amino-1,1'-biphenyl)]palladium(II) | Xphos Pd G2 | 1310584-14-5 |
| Chloro(2-dicyclohexylphosphino-2',6'-dimethoxy-1,1'-biphenyl)[2-(2'-amino-1,1'-biphenyl)]palladium(II) | SPhos Pd G2 | 1375325-64-6 |
| Chloro(2-dicyclohexylphosphino-2',6'-diisopropoxy-1,1'-biphenyl)[2-(2'-amino-1,1'-biphenyl)]palladium(II) | RuPhos Pd G2 | 1375325-68-0 |
| Chloro[(2-dicyclohexylphosphino-2',6'-bis(N,N-dimethylamino)-1,1'-biphenyl)-2-(2'-amino-1,1'-biphenyl)]palladium(II) | CPhos-Pd-G2 | |
| [(2-Dicyclohexylphosphino-2',6'-bis(N,N-dimethylamino)-1,1'-biphenyl)-2-(2'-amino-1,1'-biphenyl)] palladium(II) methanesulfonate | CPhos-Pd-G3 | |
| [(2-Di-tert-butylphosphino-2',4',6'-triisopropyl-1,1'-biphenyl)-2-(2'-amino-1,1'-biphenyl)] palladium(II) methanesulfonate | tBuXPhos-Pd-G3 | |
| (2-Dicyclohexylphosphino-2',6'-diisopropoxy-1,1'-biphenyl)[2-(2'-amino-1,1'-biphenyl)]palladium(II) methanesulfonate | RuPhos-Pd-G3 | |
| (2-Dicyclohexylphosphino-2',4',6'-triisopropyl-1,1'-biphenyl)[2-(2'-amino-1,1'-biphenyl)]palladium(II) methanesulfonate | XPhos-Pd-G3 | |
| [(2-Di-cyclohexylphosphino-3,6-dimethoxy-2',4',6'-triisopropyl-1,1'-biphenyl)-2-(2'-amino-1,1'-biphenyl)]palladium(II) methanesulfonate | BrettPhos-Pd-G3 | |
| [(2-{Bis[3,5-bis(trifluoromethyl)phenyl]phosphine}-3,6-dimethoxy-2',4',6'-triisopropyl-1,1'-biphenyl)-2-(2'-amino-1,1'-biphenyl)]palladium(II) methanesulfonate | JackiePhos-Pd-G3 | |
| Me4-tert-butyl XPhos-AuMeCN SbF6 | | 1334547-72-6 |
| tBuXPhos Au(MeCN)SbF$_6$ | | 1140531-94-7 |
| RuPhos Au(MeCN)SbF$_6$ | | |
| SPhos Au(MeCN)SbF$_6$ | | 1236160-37-4 |
| XPhos Au(MeCN)SbF$_6$ | | 1215877-64-7 |
| Me4-tert-butyl XPhos-AuCl | | 1140907-91-0 |
| tBuXPhos AuCl | | |
| RuPhos AuCl | | 1261452-57-6 |
| SPhos AuCl | | 854045-95-7 |
| CyJohnPhos AuCl | | 854045-92-4 |
| BrettPhos AuCl | | 1334547-75-9 |
| JohnPhos AuNTf$_2$ | | 1036000-94-8 |
| Me$_4$-tert-butyl XPhos-AuNTf$_2$ | | |
| tBuXphos AuNTf$_2$ | | 1190991-33-3 |
| SPhos AuNTf$_2$ | | 1121960-90-4 |
| CyJohnPhos AuNTf$_2$ | | 1016161-75-3 |
| CPhos AuNTf$_2$ | | |
| RuPhos AuNTf$_2$ | | |
| BrettPhos AuNTf$_2$ | | 1296269-97-0 |
| DavePhos AuNTf$_2$ | | 1188507-66-5 |
| CPhos | | 1160556-64-8 |
| Chloro(sodium-2-dicyclohexylphosphino-2',6'-dimethoxy-1,1'-biphenyl-3'-sulfonate)[2-(2'-amino-1,1'-biphenyl)]palladium(II) | | |
| Di-Ad-BrettPhos | | 1160861-59-5 |
| Dicyclohexyl(2-(2-methoxynaphthalen-1-yl)phenyl)phosphine | | 1309570-98-6 |
| tert-BuBrettPhos-Pd-G3 | | |
| di-Ad-Johnphos-G3 | | |

Scheme 7:

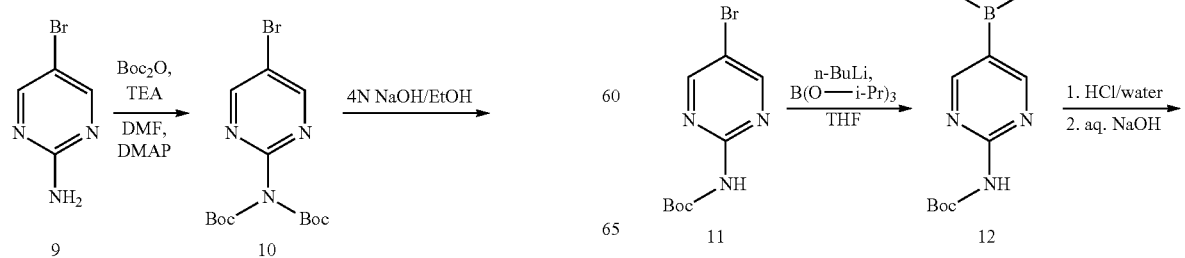

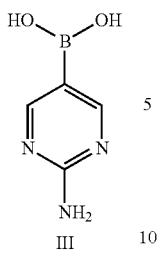

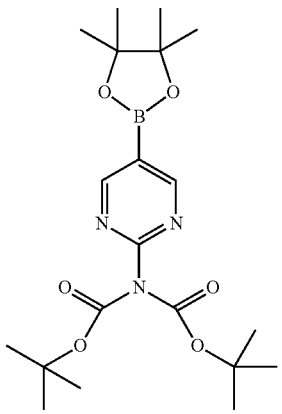

Scheme 7 shows the synthesis of 2-aminopyrimidin-5-yl-boronic acid III from 5-bromopyrimidin-2-amine 9. Protection of the 2-amino group with a Boc-protecting reagent such as di-tert-butyl dicarbonate (Boc$_2$O) proceeded through the bis-Boc-protected intermediate, bis-tert-butyl 5-bromopyrimidin-2-yl-dicarbamate 10 (Example 14) followed by basic hydrolysis of one Boc group to give mono-Boc protected, tert-butyl 5-bromopyrimidin-2-ylcarbamate 11 (Example 15). Basic hydrolysis can be conducted with an alkali earth metal hydroxide such as potassium hydroxide, sodium hydroxide, or lithium hydroxide. Metallation of 11 with an alkyl lithium reagent, such as n-butyllithium, and borylation with a trialkyl borate reagent, such as triisopropyl borate, gives 2-(tert-butoxycarbonylamino)pyrimidin-5-ylboronic acid 12 (Example 16). Deprotection by aqueous acidic hydrolysis and basification or neutralization gave III (Example 17).

Scheme 8:

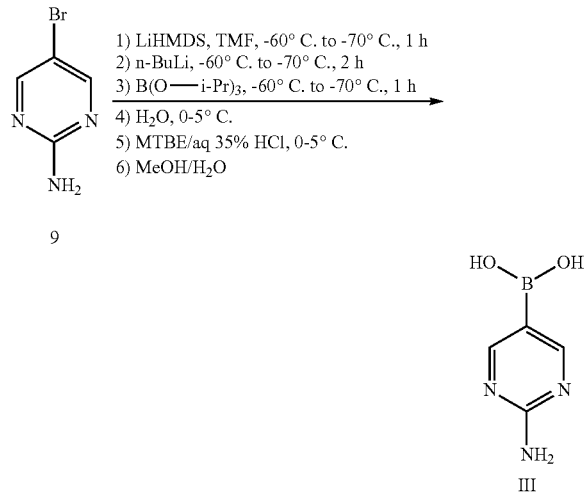

Scheme 8 shows an alternate synthesis of 2-aminopyrimidin-5-ylboronic acid III from 5-bromopyrimidin-2-amine 9. Metallation of the bromo of unprotected 9 with n-butyllithium and borylation with triisopropyl borate gave III (Example 17).

Another alternate synthesis of 2-aminopyrimidin-5-ylboronic acid III may be conducted by reaction of bis-tert-butyl 5-bromopyrimidin-2-yl-dicarbamate 10 and 4,4,4',4',5,5,5',5'-octamethyl-2,2'-bi(1,3,2-dioxaborolane), also known as: bis(pinacolato)diboron, B$_2$Pin$_2$, pinacol diborane, under Buchwald palladium catalysis conditions with the Buchwald pre-catalyst palladacycle and ligand reagents of Table 1 (Example 18) to give bis-tert-butyl 5-(4,4,5,5-tetramethyl-1,3,2-dioxaborolan-2-yl)pyrimidin-2-yldicarbamate 13.

Acidic hydrolysis of both Boc groups and the pinacol group gives 2-aminopyrimidin-5-ylboronic acid III.

Formulations

GDC-0980 may be formulated in accordance with standard pharmaceutical practice for use in a therapeutic combination for therapeutic treatment (including prophylactic treatment) of hyperproliferative disorders in mammals including humans. The invention provides a pharmaceutical composition comprising GDC-0980 in association with one or more pharmaceutically acceptable carrier, glidant, diluent, or excipient.

Suitable carriers, diluents, glidants, and excipients are well known to those skilled in the art and include materials such as carbohydrates, waxes, water soluble and/or swellable polymers, hydrophilic or hydrophobic materials, gelatin, oils, solvents, water and the like.

The formulations may be prepared using conventional dissolution and mixing procedures. The compound of the present invention is typically formulated into pharmaceutical dosage forms to provide an easily controllable dosage of the drug and to enable patient compliance with the prescribed regimen.

The pharmaceutical composition (or formulation) may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration with pharmaceutically acceptable diluents, carriers, excipients, glidants or stabilizers (Remington's Pharmaceutical Sciences (1995) 18th edition, Mack Publ. Co., Easton, Pa.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8.

The pharmaceutical formulation is preferably sterile. In particular, formulations to be used for in vivo administration must be sterile. Such sterilization is readily accomplished by filtration through sterile filtration membranes.

The pharmaceutical formulation ordinarily can be stored as a solid composition, a tablet, a pill, a capsule, a lyophilized formulation or as an aqueous solution.

The pharmaceutical formulations of the invention will be dosed and administered in a fashion, i.e., amounts, concentrations, schedules, course, vehicles and route of administration, consistent with good medical practice. Factors for consideration in this context include the particular disorder being treated, the clinical condition of the individual patient, the cause of the disorder, the site of delivery of the agent, the method of administration, the scheduling of administration, and other factors known to medical practitioners.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl, ethanol, or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, including Tween 80, PLURONICS™ or polyethylene glycol (PEG), including PEG400. The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 18th edition, (1995) Mack Publ. Co., Easton, Pa. Other examples of drug formulations can be found in Liberman, H. A. and Lachman, L., Eds., Pharmaceutical Dosage Forms, Marcel Decker, Vol 3, $2^{nd}$ Ed., New York, N.Y.

Pharmaceutically acceptable glidants may be selected from silicon dioxide, powdered cellulose, microcrystalline cellulose, metallic stearates, sodium aluminosilicate, sodium benzoate, calcium carbonate, calcium silicate, corn starch, magnesium carbonate, asbestos free talc, stearowet C, starch, starch 1500, magnesium lauryl sulfate, magnesium oxide, and combinations thereof.

The pharmaceutical formulations include those suitable for the administration routes detailed herein. The formulations may conveniently be presented in unit dosage form and may be prepared by any of the methods well known in the art of pharmacy. Techniques and formulations generally are found in Remington's Pharmaceutical Sciences $18^{th}$ Ed. (1995) Mack Publishing Co., Easton, Pa. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Pharmaceutical compositions may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may be a solution or a suspension in a non-toxic parenterally acceptable diluent or solvent, such as a solution in 1,3-butanediol or prepared from a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

EXAMPLES

Example 1

7-Methylthieno[3,2-d]pyrimidine-2,4(1H,3H)-dione VIII

Methyl 3-amino-4-methylthiophene-2-carboxylate IX (100 g, 0.584 mol) and acetic acid (750 mL, 13.1 mol) were stirred for 5 min to obtain a clear solution. A solution of potassium cyanate (56.8 g, 0.70 mol) in water (120 mL) was slowly added over 20 min, and the mixture was stirred for 1.5 h. Additional potassium cyanate (56.8 g, 0.70 mol) in water (120 mL) was slowly added over 20 min and the mixture was stirred for 2 h. Water (600 mL) was added and the mixture was cooled to 10° C. and stirred for 2 h. The solid was collected by filtration and washed with cold water (250 mL). The solid was then stirred for 12 h in a solution of sodium hydroxide (79.4 g, 1.99 mol) in water (1.4 L). The pH was adjusted to 6-7 by slow addition of aqueous concentrated hydrochloric acid solution (35 wt %, 110 mL) and was then stirred for 5 min. The resulting solid was collected by filtration, washed with water (2×250 mL) and dried under reduced pressure at 50° C. for 24 h to afford 7-methylthieno[3,2-d]pyrimidine-2,4(1H, 3H)-dione VIII as an off-white solid (89.6 g, 84% yield). $^1$H NMR (500 MHz, DMSO-$d_6$) δ 7.68 (s, 1H), 2.20 (s, 3H); LCMS (ESI pos) m/z [M+H] 183.

Example 2

2,4-Dichloro-7-methylthieno[3,2-d]pyrimidine VII

To a mixture of 7-methylthieno[3,2-d]pyrimidine-2,4(1H, 3H)-dione VIII (89.4 g, 0.491 mol) and N,N-dimethylaniline (44.6 g, 0.368 mol) in acetonitrile (450 mL) was added phosphorus oxychloride (312 g, 2.04 mol) over 10 min. The reaction mixture was heated to 85° C. and stirred for 24 h. After being cooled to rt, the mixture was slowly transferred into a mixture of ice (900 g) and water (300 mL) while maintaining the temperature below 10° C. The mixture was stirred at that temperature for 30 min. The solid was collected by filtration, washed with water (450 mL) and dried under reduced pressure at 50° C. for 24 h to afford 2,4-dichloro-7-methylthieno [3,2-d]pyrimidine VII as an off-white solid (97.0 g, 90% yield). $^1$H NMR (400 MHz, CDCl$_3$) δ 7.75 (s, 1H), 2.50 (s, 3H); LCMS (ESI pos) m/z [M+H] 220.

Example 3

4-(2-Chloro-7-methylthieno[3,2-d]pyrimidin-4-yl)morpholino VI

A mixture of 2,4-dichloro-7-methylthieno[3,2-d]pyrimidine VII (90 g, 0.411 mol) and methanol (900 mL) was cooled to 10° C. Morpholine (89.5 g, 1.03 mol) was added while maintaining the temperature below 15° C. The reaction mixture was stirred for 2 h and then cooled to 5° C. and stirred for additional 1 h. The solid was collected by filtration, washed with water (450 mL) and dried under reduced pressure at 50° C. for 24 h to afford 4-(2-chloro-7-methylthieno[3,2-d]pyrimidin-4-yl)morpholino VI as a white solid (105 g, 95% yield). $^1$H NMR (400 MHz, CDCl$_3$) δ 7.94 (s, 1H), 3.95-3.86 (m, 4H), 3.80-3.71 (m, 4H), 2.9 (s, 3H); LCMS (ESI pos) m/z [M+H] 270

Example 4

2-Chloro-7-methyl-4-morpholinothieno[3,2-d]pyrimidine-6-carbaldehyde IV 4-(2-Chloro-7-methylthieno[3,2-d]pyrimidin-4-yl)morpholine VI (27.0 g, 100 mmol) was charged to a suitably sized reactor and tetrahydrofuran (anhydrous, 270 mL) was added. The reaction mixture was cooled to below −10° C., and a 20 wt % solution of i-PrMgCl in tetrahydrofuran (25.7 g, 50.0 mmol) was slowly added, followed by a slow addition of a 25 wt % solution of n-BuLi in heptane (30.0 g, 117 mmol) while an internal temperature below −10° C. was maintained. The mixture was allowed to stir at below −10° C. for 2 h. Anhydrous N,N-dimethylformamide (14.6 g, 200 mmol) was slowly added while keeping the internal temperature below −10° C. The reaction mixture was stirred for 1-2 h, transferred to a mixture of 80% acetic acid, 37% aqueous hydrochloric acid, isopropanol and water. The resulting slurry was heated to 50-55° C. and stirred for 1-3 h. The suspension was concentrated under reduced pressure to remove tetrahydrofuran. The suspension was then cooled to rt, filtered and rinsed with water. The cake was dried under reduced pressure at 40-60° C. to afford 2-chloro-7-methyl-4-morpholinothieno[3,2-d]pyrimidine-6-carbaldehyde IV as a yellow solid (29.2 g, 98% yield). $^1$H NMR (400 MHz, CDCl$_3$) δ 10.38 (s, 1H), 4.03-4.05 (m, 4H), 3.85-3.87 (m, 4H), 2.76 (s, 3H)

Example 5

(S)-1-(4-((2-Chloro-7-methyl-4-morpholinothieno[3,2-d]pyrimidin-6-yl)methyl)piperazin-1-yl)-2-hydroxypropan-1-one II Method A: 2-Chloro-7-methyl-4-morpholinothieno[3,2-d]pyrimidine-6-carbaldehyde IV (68.9 g, 231 mmol) was charged to a suitably sized reactor, followed by acetonitrile (870 mL), (S)-2-hydroxy-1-(piperazin-1-yl)propan-1-one oxalate (V) (86.2 g, 347 mmol), sodium acetate (57.0 g, 695 mmol) and glacial acetic acid (6.90 g, 115 mmol). Molecular sieve 3 Å powder (75 g) was added to the reactor, and the slurry was heated to 80° C. and stirred for a minimum of 2 h. The mixture was cooled to 40° C. and sodium triacetoxyborohydride (59.0 g, 278 mmol) was added. After being stirred for 2 h, water (690 mL) and CELITE® (35 g) were slowly added and the mixture was heated to 50° C. and stirred for 1 h, filtered and rinsed with acetonitrile (210 mL). The filtrate was concentrated under reduced pressure to remove acetonitrile. Toluene (689 mL) was added and the pH was adjusted to 7.5-8.0 with 10% aqueous sodium carbonate solution. The organic phase was separated, extracted with a mixture of water and sulfuric acid. The aqueous phase was separated and toluene (483 mL) was added. The pH was adjusted to 7.5-8.0 with 10% aqueous sodium carbonate solution. The mixture was warmed to 20° C. and the organic phase was separated, concentrated under reduced pressure to remove acetonitrile, flushed with toluene and the resulting mixture was cooled to 0-5° C. n-Heptane (344 mL) was slowly added and the resulting slurry was filtered and rinsed a mixture of toluene and n-heptane. The cake was dried under reduced pressure to afford (S)-1-(4-((2-chloro-7-methyl-4-morpholinothieno[3,2-d]pyrimidin-6-yl)methyl)piperazin-1-yl)-2-hydroxypropan-1-one II (76.3 g, 75% yield). $^1$H NMR (300 MHz, DMSO-d$_6$) δ 4.84 (d, J=6.80 Hz, 1H), 4.37-4.47 (m, 1H), 3.79-3.97 (m, 4H), 3.65-3.78 (m, 4H) 3.35-3.64 (m, 4H), 3.30 (s, 2H), 2.33-2.64 (m, 4H), 2.24 (s, 3H), 1.17 (d, J=6.80 Hz, 3H)

Method B: 2-Chloro-7-methyl-4-morpholinothieno[3,2-d]pyrimidine-6-carbaldehyde IV (14.9 g, 50.0 mmol.) was charged to a suitably sized reactor, followed by methanol (298 mL), (S)-2-hydroxy-1-(piperazin-1-yl)propan-1-one oxalate V (18.6 g, 74.9 mmol), sodium acetate (12.3 g, 150 mmol), glacial acetic acid (3.0 g, 50.0 mmol) and trimethylorthoformate (53.1 g, 500 mmol). The slurry was heated to 55-60° C. and stirred for 4 hr. A 30% solution of 2-picolineborane in THF (21.4 g, 60.0 mmol) was slowly added and the slurry was stirred for 1-2 h. The reaction mixture was partially concentrated under reduced pressure. Toluene (230 mL) was added and the reaction mixture was concentrated under reduced pressure. Toluene (114 mL) was added and the reaction mixture was again partially concentrated under reduced pressure. To the residue was added toluene (218 mL) and the mixture was cooled to 20-30° C. Water (431 mL) was added and the pH was adjusted to 7.5-8.5 with 10% aqueous sodium carbonate solution (162 mL). The organic phase was separated, cooled to 0-5° C. and extracted with a mixture of water (180 mL) and 96% sulfuric acid (6.1 g). The aqueous phase was separated and toluene (118 mL) was added. The pH was adjusted to 7.5-8.5 with 10% aqueous sodium carbonate solution (110 mL) at 0-5° C. The mixture was warmed to 20° C. and the organic phase was separated. The organic phase was diluted with toluene (100 mL) and concentrated under reduced pressure to its original volume (approximately 150 mL). The solution was warmed to 53-57° C., and n-heptane (26 mL) was added. The solution was seeded with (S)-1-(4-((2-chloro-7-methyl-4-morpholinothieno[3,2-d]pyrimidin-6-yl)methyl)piperazin-1-yl)-2-hydroxypropan-1-one II and the suspension was stirred at 53-57° C. for 30 min. Heptane (82 mL) was slowly added and the resulting slurry was cooled to 0-5° C., filtered and washed with a mixture of toluene and n-heptane and subsequently with n-heptane. The cake was dried at 30-45° C. under reduced pressure to afford (S)-1-(4-((2-chloro-7-methyl-4-morpholinothieno[3,2-d]pyrimidin-6-yl)methyl)piperazin-1-yl)-2-hydroxypropan-1-one II (18.6 g, 84% yield)

Method C: 2-Chloro-7-methyl-4-morpholinothieno[3,2-d]pyrimidine-6-carbaldehyde IV (15.0 g, 50 mmol) was charged to a suitably sized reactor, followed by methanol (306 mL), (S)-2-hydroxy-1-(piperazin-1-yl)propan-1-one oxalate V (18.8 g, 75 mmol), N-methyl morpholine (10.2 g, 100 mmol) and trimethylorthoformate (53.1 g, 500 mmol). The slurry was heated to 55-60° C. and stirred for 4 hrs. 5-Ethyl-2-methylpyridine borane (8.7 g, 60.0 mmol) were slowly added and the solution was stirred for 2 h. The reaction mixture was partially concentrated under reduced pressure. Me-THF (350 mL) was added and the reaction mixture was concentrated under reduced pressure to an end volume of 300 mL. The mixture was cooled to 5° C. 3.3% Sulfuric acid in water (401 g) was added and pH 1.6 was reached. The organic phase was removed. The pH of the aqueous phase was adjusted to 7.9 with 10% aqueous sodium carbonate solution (300 g) at 0-5° C. The mixture was warmed to 25° C. and the organic phase was separated. The organic phase was concentrated under reduced pressure to 75 mL. The solution was warmed to 35° C. and seeded with 41 mg (S)-1-(4-((2-chloro-7-methyl-4-morpholinothieno[3,2-d]pyrimidin-6-yl)methyl) piperazin-1-yl)-2-hydroxypropan-1-one II. The suspension was cooled to 0° C. and n-heptane (200 g) was added. The resulting slurry was aged at −5° C., filtered and washed with n-heptane. The cake was dried at 70° C. under reduced pressure to afford (S)-1-(4-((2-chloro-7-methyl-4-morpholinothieno[3,2-d]pyrimidin-6-yl)methyl)piperazin-1-yl)-2-hydroxypropan-1-one II (17.8 g, 81% yield)

Example 6

(S)-1-Chloro-1-oxopropan-2-yl acetate 3

A solution of (S)-2-hydroxypropanoic acid (L-lactic acid) 1 (35.0 kg, 388 mol) in dichloromethane (50.0 kg) was cooled to 5-10° C. and acetyl chloride (75.0 kg, 955 mol) was added while maintaining the reaction temperature at 10-20° C. The reaction mixture was stirred at 10-20° C. for 4 h. Dichloromethane (240 kg) was added followed by oxalyl chloride (139 kg, 1095 mol) at a rate to maintain the reaction temperature at 0-15° C. The reaction mixture was aged at 10-20° C. for 10 h and the mixture was concentrated under reduced pressure to give a residue containing (S)-1-chloro-1-oxopropan-2-yl acetate 3.

Example 7

(S)-1-(4-Benzylpiperazin-1-yl)-1-oxopropan-2-yl acetate 4

In a vessel was charged dichloromethane (260 kg) followed by addition of triethylamine (65.0 kg, 642 mol). The mixture was cooled to 0-10° C. and 4-benzylpiperazine dihydrochloride (31.8 kg, 128 mol) was added. To the mixture was added (S)-1-chloro-1-oxopropan-2-yl acetate 3 from Example 6 while maintaining the reaction temperature at 5-15° C. The reaction mixture was stirred at 10-20° C. for 10 h. Ice-water (50 kg) was added and the layers were separated. The aqueous layer was extracted with dichloromethane (2×50 kg). The organic layers were combined and cooled to 5-10° C. Aqueous HCl (4N) solution was slowly added to adjust the pH to 6-7. The layers were separated and the aqueous layer was extracted with dichloromethane (2×50 kg). The organic layers were combined, dried over anhydrous sodium sulfate, filtered and concentrated under reduced pressure to give a residue containing (S)-1-(4-benzylpiperazin-1-yl)-1-oxopropan-2-yl acetate 4.

Example 8

(S)-1-(4-Benzylpiperazin-1-yl)-2-hydroxypropan-1-one 5

Methanol (300 kg) was added to the residue from Example 7 containing (S)-1-(4-benzylpiperazin-1-yl)-1-oxopropan-2-yl acetate 4 and the mixture was cooled to 0-10° C. A solution of lithium hydroxide monohydrate (13.6 kg, 324 mol) in water (100 kg) was added at a rate to maintain the reaction temperature at 0-15° C. After aging for 2 h, the pH was adjusted to 7 at 5-15° C. with acetic acid (4.5 kg, 75 mol). The mixture was concentrated under reduced pressure. To the residue was added dichloromethane (150 kg) and the layers were separated. The aqueous layer was extracted with dichloromethane (2×150 kg). The organic layers were combined, dried over anhydrous sodium sulfate, filtered and concentrated under reduced pressure. Ethyl acetate (31 kg) was added to the residue, followed by slow addition of cyclohexane (183 kg). The mixture was heated to 40-50° C. and stirred for 1 h. The mixture was cooled to 0-10° C. and aged for 8 h. The solid was collected by filtration, washed with cold cyclohexane and dried under reduced pressure at 50° C. for 12 h to afford (S)-1-(4-benzylpiperazin-1-yl)-2-hydroxypropan-1-one 5 (46 kg, 71% yield, 98% purity by HPLC). $^1$H NMR (300 MHz, CDCl3) δ 7.42-7.20 (m, 5H), 4.43 (q, J=6.4 Hz, 1H), 3.84 (broad s, 1H), 3.76-3.55 (m, 2H), 3.53 (s, 2H), 3.48-3.32 (m, 2H), 2.46 (s, 4H), 1.32 (dd, J=6.6, 3.9 Hz, 3H).

Example 9

Oxalate salt of (S)-2-hydroxy-1-(piperazin-1-yl)propan-1-one V

Ethanol (350 kg), Palladium (10% on activated carbon) (8.40 kg, 7.89 mol) and (S)-1-(4-benzylpiperazin-1-yl)-2-hydroxypropan-1-one 5 (70.0 kg, 282 mol) were charged to a reactor and the mixture was purged with nitrogen and heated to reflux. Cyclohexene (70.0 kg, 852 mol) was slowly added. The reaction mixture was heated to reflux and stirred for 24 h. After cooling to ambient temperature, the mixture was filtered through a pad of CELITE® and the cake was washed with ethanol (20 kg). The filtrate was cooled to 10-15° C. and a solution of oxalic acid dihydrate (36.0 kg, 286 mol) in tetrahydrofuran (156 kg) was slowly added at a rate to maintain the reaction temperature at 10-20° C. After aging for 2 h, the solid was collected by filtration, washed with ethanol (100 kg) and dried under reduced pressure at 50-55° C. to afford (S)-2-hydroxy-1-(piperazin-1-yl)propan-1-one oxalate salt V (58.2 kg, 83%). $^1$H NMR (300 MHz, D$_2$O) δ 4.73-4.51 (m, 1H), 3.93-3.59 (m, 4H), 3.26 (dd, J=8.8, 4.0 Hz, 4H), 1.27 (d, J=6.7 Hz, 3H).

Example 10

(S)-1-(4-Benzylpiperazin-1-yl)-2-hydroxypropan-1-one 8

A flask charged with 1-benzylpiperazine (5.0 g, 28.40 mmol 1.00 equiv) was cooled to 10° C. Ethyl (2S)-2-hydroxypropanoate 7 (10.1 g, 85.1 mmol, 3.00 equiv) was added at a rate to keep the temperature below 20° C. Sodium methoxide (25 wt % in MeOH) (4.9 mL, 21.3 mmol, 0.75 equiv) was added while maintaining the temperature below 20° C. The cold water bath was removed and the reaction mixture was allowed to warm to ambient temperature and aged for 16 h. The mixture was diluted with ethanol (25 mL) and treated with AMBERLITE® IRC-748 resin (Dow Chemical Co., Na$^+$ form 31.6 g, 1.8 meq/g, 2 equiv, pre-conditioned to H$^+$ form using 5% aq HCl). The suspension was stirred at ambient temperature for 2 h. The resin was removed by filtration through a pad of CELITE® (3.5 g) and the pad was washed with ethanol (2×33.8 mL). The filtrate and washes were combined and concentrated under reduced pressure to 50 mL. To the solution was added activated charcoal (DARCO® KB-WJ, Norit Inc., 50 wt % based on 100% theoretical yield of product, 3.52 g). The suspension was stirred at ambient temperature for 18 h. The suspension was filtered through a pad of CELITE® (7 g) and the pad was washed with EtOH (2×33.6 mL). The filtrate and washes were combined and concentrated under vacuum to afford a residue containing (S)-1-(4-benzylpiperazin-1-yl)-2-hydroxypropan-1-one 8.

Example 11

Oxalate salt of (S)-2-hydroxy-1-(piperazin-1-yl)propan-1-one V

Method A: Hydrogen gas hydrogenolysis—To the residue containing (S)-1-(4-benzylpiperazin-1-yl)-2-hydroxypropan-1-one 8 from Example 10 was added ethanol (22.5 mL) and palladium (10% on activated carbon, 56.14% water wetted) (2.07 g, 0.85 mmol, 0.03 equiv). The mixture was purged with argon and the vessel was charged with hydrogen to 50 psi. The mixture was stirred under hydrogen at 40° C. for 21 h. After cooling to ambient temperature, the mixture was filtered through a pad of CELITE® (7 g) and washed with ethanol (33 mL). The filtrate and wash were combined and concentrated under reduced pressure to afford a residue containing crude (S)-2-hydroxy-1-(piperazin-1-yl)propan-1-one 6 as an oil. The crude (S)-2-hydroxy-1-(piperazin-1-yl)propan-1-one 6 was dissolved in a 50:50 (v/v) mixture of ethanol/tetrahydrofuran (17.5 mL each) and cooled to 10° C. A solution of oxalic acid dihydrate (7.17 g, 56.8 mmol, 2 equiv) in a 50:50 (v/v) mixture of ethanol:tetrahydrofuran (14 mL each) was slowly added. The suspension was allowed to warm to ambient temperature and aged for 18 h. The suspension was cooled to 10° C. and the solid collected by filtration, washed with cold ethanol (2×27.5 mL), dried under reduced pressure at 40° C. for 24 h to afford the oxalate salt of (S)-2-hydroxy-1-(piperazin-1-yl)propan-1-one V as a white solid (5.24 g, 74%).

Method B: Transfer hydrogenolysis—The residue containing (S)-1-(4-benzylpiperazin-1-yl)-2-hydroxypropan-1-one 8 from Example 10 was diluted with ethanol (22.5 mL) and the solution was degassed three times through a nitrogen and vacuum cycle. Palladium (10% on activated carbon, 56.14% water wetted) (2.07 g, 0.85 mmol, 0.03 equiv) was added and the mixture was degassed five times through a nitrogen and vacuum cycle. The mixture was heated to 55° C. and cyclohexene (11.6 g, 142 mmol, 5.00 equiv) was slowly added. The reaction mixture was heated to reflux and stirred for 6 h. After cooling to ambient temperature, the mixture was filtered through a pad of CELITE® (14 g), washed with ethanol (33 mL). The filtrate and wash were combined and concentrated under reduced pressure to afford a residue containing (S)-2-hydroxy-1-(piperazin-1-yl)propan-1-one 6 as an oil which was dissolved in a 50:50 (v/v) mixture of ethanol:tetrahydrofuran (35 mL each) and cooled to 10° C. A solution of oxalic acid dihydrate (7.17 g, 56.8 mmol, 2 equiv) in a 50:50 (v/v) mixture of ethanol:tetrahydrofuran (14 mL each) was slowly added. The suspension was allowed to warm to ambient temperature and aged for 18 h. The suspension was cooled to 10° C. and the solid was collected by filtration. The solid was washed with cold ethanol (2×27.5 mL) and dried under vacuum at 40° C. for 24 h to afford the oxalate salt of (S)-2-hydroxy-1-(piperazin-1-yl)propan-1-one V as a white solid (4.16 g, 59%). $^1$H NMR (300 MHz, D$_2$O) δ 4.73-4.51 (m, 1H), 3.93-3.59 (m, 4H), 3.26 (dd, J=8.8, 4.0 Hz, 4H), 1.27 (d, J=6.7 Hz, 3H).

Example 12

Oxalate salt of (S)-2-hydroxy-1-(piperazin-1-yl)propan-1-one V

A flask charged with piperazine (10.0 g, 116 mmol) and (S)-ethyl 2-hydroxypropanoate 7 (17.84 g, 151 mmol, 1.30 equiv) was cooled to 10° C. Sodium methoxide (25 wt % in MeOH) (12.55 g, 58.1 mmol, 0.50 equiv) was slowly added while maintaining the temperature below 20° C. The cold water bath was removed and the reaction mixture was allowed to warm to ambient temperature and aged for 19 h. Water (6.23 g, 346 mmol, 3.0 equiv) was added and the mixture was aged for 16 h. The mixture was diluted with ethanol (40 mL) and concentrated under reduced pressure. The residue was diluted with ethanol (40 mL) and treated with a solution of oxalic acid dihydrate (6.58 g, 52.2 mmol) in ethanol (30 mL) to adjust the pH to 7.5. The suspension was cooled to <10° C., filtered through a pad of CELITE® and washed with ethanol (2×60 mL). The filtrate and washes were combined and concentrated to 50 mL. The solution was cooled to 10° C. and a solution of oxalic acid dihydrate (16.1 g, 128 mmol) in ethanol (60 mL) was slowly added. The suspension was allowed to warm to ambient temperature and stirred for 1 h. The suspension was cooled to 10° C. and the solid was collected by filtration, washed with cold ethanol (2×18 mL) and dried under reduced pressure at 50° C. for 24 h to afford the oxalate salt of (S)-2-hydroxy-1-(piperazin-1-yl)propan-1-one V as a white solid (15.2 g, 53%). $^1$H NMR (300 MHz, D$_2$O) δ 4.73-4.51 (m, 1H), 3.93-3.59 (m, 4H), 3.26 (dd, J=8.8, 4.0 Hz, 4H), 1.27 (d, J=6.7 Hz, 3H).

Example 13

(S)-1-(4-((2-(2-Aminopyrimidin-5-yl)-7-methyl-4-morpholinothieno[3,2-d]pyrimidin-6-yl)methyl)piperazin-1-yl)-2-hydroxypropan-1-one, GDC-0980, Formula I Method A: (S)-1-(4-((2-chloro-7-methyl-4-morpholinothieno[3,2-d]pyrimidin-6-yl)methyl)piperazin-1-yl)-2-hydroxypropan-1-one II (22.0 g, 50.0 mmol) was charged to a suitably sized reactor, followed by n-propanol (198 mL), 2-aminopyrimidin-5-ylboronic acid III (8.30 g, 59.7 mmol) and potassium phosphate (21.3 g, 100 mmol). The resulting mixture was degassed by vacuum/argon purge three times. Bis(triphenylphosphine)palladium (II) chloride (0.053 g, 0.076 mmol) was added and the slurry was again degassed by vacuum/argon purge three times. The mixture was heated within 2 h to 85° C. and stirred for 30 min. The reaction mixture was cooled to rt, water (200 mL) was added and the pH was adjusted to 6.0-8.0 with 37 wt % aqueous hydrochloric acid solution (6.92 mL). The biphasic mixture was heated to 80° C. and stirred for 1 h. The organic phase was separated and slowly filtered over a preheated pressure filter loaded with a ZETACARBON® R55SP pad (Cuno Inc., a 3M Company, Meriden Conn.). The filter unit was washed with a warm (80° C.) mixture of n-propanol (45 mL) and water (24 mL). The filtrate was concentrated under reduced pressure while keeping the volume constant by addition of water (150 mL). The resulting slurry was cooled to 26-36° C., filtered and rinsed with a mixture of n-propanol (15 mL) and water (108 mL). The cake was dried under reduced pressure at 45° C. to afford the crude product as a yellowish white solid (20.7 g). The crude product was charged to a suitably sized reactor, followed by n-propanol (116 mL) and water (62 mL). The suspension was heated to 85° C. and stirred to afford a clear solution. The solution was filtered over a preheated polishing filter unit and rinsed with a mixture of n-propanol (23 mL) and water (12 mL). The filtrate was cooled to −10° C., aged for 1 h and filtered. The filter cake was washed with n-propanol (77 mL) and dried under reduced pressure at 60-70° C. to afford (S)-1-(4-((2-(2-aminopyrimidin-5-yl)-7-methyl-4-morpholinothieno[3,2-d]pyrimidin-6-yl)methyl)piperazin- 1-yl)-2-hydroxypropan-1-one, GDC-0980, Formula I as a yellowish white to white solid (18.9 g, 76%). $^1$H NMR (400 MHz, DMSO-d$_6$) δ 9.15 (s, 2H), 7.05 (s, 2H), 4.84 (d, J=6.98 Hz, 1H), 4.35-4.48 (m, 1H), 3.89-4.00 (m, 4H), 3.84 (s, 2H), 3.67-3.78 (m, 4H), 3.36-3.64 (m, 4H), 2.38-2.60 (m, 4H), 2.34 (s, 3H), 1.18 (d, J=6.53 Hz, 3H)

Method B: (S)-1-(4-((2-chloro-7-methyl-4-morpholinothieno[3,2-d]pyrimidin-6-yl)methyl)piperazin-1-yl)-2-hydroxypropan-1-one II (33.0 g, 75 mmol) was charged to a suitably sized reactor, followed by n-propanol (337 g), water (450 g), 2-aminopyrimidin-5-ylboronic acid III (12.5 g, 90 mmol) and dipotassium hydrogen phosphate (39.2 g, 225 mmol). The resulting mixture was degassed by vacuum/argon purge three times. Bis(triphenylphosphine)palladium (II) chloride (0.079 g, 0.112 mmol) was added and the slurry was again degassed by vacuum/argon purge three times. The mixture was heated within 2 h to 65° C. and stirred for 10 hours. The organic phase was separated and slowly filtered over a preheated pressure filter loaded with a ZETACARBON® R55SP pad (Cuno Inc., a 3M Company, Meriden Conn.). The filter unit was washed with a warm (80° C.) n-propanol (45 mL). Water (750 mL) were added to the filtrate and the resulting suspension was cooled to 10° C., aged for 1 h and filtered. The filter cake was washed with water (150 g) and dried under reduced pressure at 45° C. to afford (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one, GDC-0980, Formula I as a white solid (30.1 g, 79%).

Example 14

Bis-tert-butyl 5-bromopyrimidin-2-yl-dicarbamate 10

To a mixture of 5-bromopyrimidine-2-amine 9 (80.0 kg, 460 mol), di-tert-butyl dicarbonate (Boc$_2$O) (250 kg, 1140 mol) and triethylamine (139 kg, 1370 mol) in dimethylformamide (DMF) (319 L) was slowly added 4-dimethylaminopyridine (DMAP) (5.70 kg, 46.6 mol). The reaction mixture was heated to 70-90° C. and stirred for 3 h. After being cooled to 15-40° C., the mixture was slowly quenched with ice-water (6000 kg) and the suspension was stirred for 1 h. The solid was collected by filtration and stirred with water (200 kg) for 1 h. The resulting solid was collected by filtration and dried under vacuum at 50° C. for 10 h to afford bis-tert-butyl 5-bromopyrimidin-2-yl-dicarbamate 10 (216 kg, >97A % by HPLC, quantitative yield). $^1$H NMR (500 MHz, CDCl$_3$) δ 8.71 (s, 2H), 1.40 (s, 18H); LCMS (ESI) m/z [M−H] 373

Example 15 tert-Butyl 5-bromopyrimidin-2-ylcarbamate 11

To a solution of 2-[bis(tert-butoxycarbonyl)amino]-5-bromopyrimidine 10 (216 kg crude, 460 mol, assuming quantitative yield in previous step) in anhydrous ethanol (1692 L) was slowly added a solution of sodium hydroxide (55.2 kg, 1380 mol) in water (344 L) while maintaining the temperature at 0-20° C. The mixture was stirred at that temperature until the content of 2-[bis(tert-butoxycarbonyl)-amino]-5-bromopyrimidine (10) was ≤0.5% by HPLC. The reaction mixture was cooled to 0-5° C. and the pH was adjusted to 7 by addition of oxalic acid (86.0 kg, 955 mol) while maintaining the temperature below 5° C. The mixture was then distilled under vacuum to a volume of 500-600 L while controlling the temperature below 50° C. Water (800 kg) was added and the mixture was stirred for 1 h. The solid was collected by filtration and stirred with water (2×500 L). The resulting solid was collected by filtration and dried under reduced pressure at 50° C. to afford tert-butyl 5-bromopyrimidin-2-ylcarbamate 11 (107 kg, 85% yield over two steps). $^1$H NMR (500 MHz, CDCl$_3$) δ 8.63 (s, 2H), 8.12 (s, 1H), 1.55 (s, 9H). LCMS (ESI) m/z [M+H-Boc] 176

Example 16

2-(tert-Butoxycarbonylamino)pyrimidin-5-ylboronic acid 12

To a mixture of tert-butyl(5-bromopyrimidin-2-yl)carbamate 11 (45.0 kg, 164 mol) in tetrahydrofuran (910 L) was slowly added triisopropyl borate (Sigma-Aldrich, CAS Number 5419-55-6, 77.4 kg, 412 mol) and the mixture was cooled to −70° C. (minus seventy degrees Celsius). n-Butyllithium (2.5 M solution in hexanes, 264 L, 660 mol) was added while maintaining the temperature below −65° C. and the reaction mixture was stirred until the content of tert-butyl(5-bromopyrimidin-2-yl)carbamate 11 was ≤0.5% by HPLC. Purified water (5 kg) was added while keeping the temperature below 40° C. The mixture was cooled to 5° C. and the pH was adjusted to 7 by addition of 25% aqueous sodium hydrogen sulfate (270 kg). The mixture was heated to 50° C. and the organic solvents were removed under reduced pressure. Water (600 kg) was added and the mixture was cooled to <5° C., and the pH was adjusted to 3.5 by addition of 25% aqueous sodium hydrogen sulfate (60 kg). The solid was collected by filtration and stirred with water (240 kg) for 30 min. The resulting solid was collected by filtration and re-slurried with water (550 kg), and the mixture was cooled to 0-5° C. 10% aqueous sodium hydroxide solution was added while maintaining the temperature below 10° C., and the mixture was stirred for 2 h. The aqueous phase was extracted with petroleum ether (2×40 kg). The pH of the aqueous phase was then adjusted to 3.5 by addition of 25% aqueous sodium hydrogen sulfate solution while keeping the temperature at 0-10° C. The slurry was filtered and the solid was re-slurried with water (400 kg) for 1 h. The solid was collected by filtration and was dried on the filter to afford the Boc protected, 2-(tert-butoxycarbonylamino)pyrimidin-5-ylboronic acid 12 (40 Kg wet, 49 wt % by HPLC, 50% yield). $^1$H NMR (500 MHz, DMSO-d$_6$) δ 10.08 (s, 1H), 8.82 (s, 2H), 8.42 (s, 2H), 1.46 (s, 9H)

Example 17

2-Aminopyrimidin-5-ylboronic acid III

To a mixture of [2-[(tert-butoxycarbonyl)amino]pyrimidin-5-yl]boronic acid 12 (40.0 kg, 49 wt % by HPLC, 82.0 mol) in water (245 kg) was added concentrated hydrochloric acid (39.6 L) while maintaining the temperature below 30° C. The reaction mixture was stirred for 12 h and was then cooled to 10° C. The pH of the mixture was adjusted to 6.5 by addition of 50% aqueous sodium hydroxide solution while maintaining the temperature below 15° C. and the mixture was then stirred for 1 h. Water (69.0 kg) was added and the mixture was aged for 30 min. The resulting slurry was filtered and the cake was dried under vacuum at 50° C. to afford 2-aminopyrimidin-5-ylboronic acid III (10.2 kg, 90% yield). $^1$H NMR (300 MHz, DMSO-d$_6$) δ 8.50 (s, 2H), 7.97 (s, 2H), 6.74 (s, 2H).

By the alternative synthetic route in Scheme 8, to a 3-L flask under nitrogen was charged tetrahydrofuran (1055 mL), followed by 5-bromopyrimidine-2-amine 9 (70.0 g, 0.40 mol). The mixture was cooled to a temperature between −60° C. and −70° C. and lithium bis(trimethylsilyl)amide (LiH-MDS) (1M in tetrahydrofuran, 483 mL, 0.483 mol) was charged over 30 min while maintaining the temperature between −60° C. and −70° C. The mixture was stirred at −60° C. to −70° C. for 1 h. n-Butyllithium (2.5 M in hexanes, 515 mL, 1.29 mol) was charged over 1 h while maintaining the temperature between −60° C. and −70° C., and the reaction mixture was then aged for 2 h. Additional n-butyllithium (2.5 M in hexanes, 48 mL, 0.12 mol) was charged over 15 min while maintaining the temperature between −60° C. and −70° C., and the reaction mixture was stirred for 1 h. To the mixture was added triisopropyl borate (91.0 g, 0.48 mol) over 1 h while maintaining the temperature between −60° C. and −70° C., and the reaction mixture was stirred for 1 h. The mixture was then allowed to warm to 0-5° C. and water (700 mL) was added over 1 h. After being aged at 0-5° C. for 30 min, the resulting layers were separated. To the aqueous layer was added water (420 mL) over 30 min, followed by addition of tert-butyl methyl ether (822 mL). The mixture was allowed to warm to 20-25° C. and was stirred for 30 min. The layers were separated and the aqueous layer was washed with tert-butyl methyl ether (5×700 mL). The aqueous layer was cooled to 0-5° C., and 35% aqueous hydrochloric acid solution (137 mL) was added over 1 h while maintaining the temperature between 0-5° C. The mixture was stirred at 0-5° C. for 1.5 h, filtered, washed with water (14 mL) and the cake was dried under vacuum at 45-50° C. to afford the crude product (26.7 g). The crude product was charged to a 5-L flask, followed by addition of methanol (908 mL), and the mixture was stirred at room temperature (rt) for 20 min. The mixture was warmed to 65° C. and stirred for 1.5 h. To the mixture was added water (2136 mL) over 2 h and the suspension was stirred for 1.5 h. The mixture was cooled to 20° C. and stirred for 14 h. The solid was collected by filtration and the filter cake was washed with water (13 mL), dried under vacuum at 45-50° C. for 12 h to afford 2-aminopyrimidin-5-ylboronic acid III (23.6 g, 42% yield)

Example 18

2-Aminopyrimidin-5-ylboronic acid III

To a solution of 2-[bis(tert-butoxycarbonyl)amino]-5-bromopyrimidine 10 (10 g, 27 mmol), Chloro(2-dicyclohexylphosphino-2',4',6'-triisopropyl-1,1'-biphenyl)[2-(2'-amino-1,1'-biphenyl)]palladium(II) (101 mg, 0.128 mmol), 4,4,4',4',5,5,5',5'-octamethyl-2,2'-bi(1,3,2-dioxaborolane), also known as: bis(pinacolato)diboron, B₂Pin₂, pinacol diborane (13.6 g, 53.4 mmol) and sodium acetate (7.9 g, 80 mmol) was added 50 mL toluene. The mixture was heated to 85° C. for 7 hours. After cooling to 20° C. 1N NaOH in water (90 mL) were added. The biphasic mixture was filtered over celite and the organic layer was discarded. The organic layer was heated to 80° C. and 37% HCl in water (21.2 g) were added. The solution was stirred for 2 hours and cooled to 0° C. To the solution 28% NaOH in water (23.7 g) were added until pH 7. The resulting suspension was filtered and rinsed with water. The off-white solid was dried under vacuum at 50° C. for 16 hours.

The resulting 4.5 g crude 2-Aminopyrimidin-5-ylboronic acid III was suspended in 144 g methanol and heated to 65° C. At this temperature water (73 g) were added. The suspension is cooled to 20° C. and filtered. The white solid was dried under vacuum at 50° C. for 16 hours to afford 2-Aminopyrimidin-5-ylboronic acid III (1.9 g, 97% (m/m) 49% yield)

Although the foregoing invention has been described in some detail by way of illustration and example for purposes of clarity of understanding, the descriptions and examples should not be construed as limiting the scope of the invention. Accordingly, all suitable modifications and equivalents may be considered to fall within the scope of the invention as defined by the claims that follow. The disclosures of all patent and scientific literature cited herein are expressly incorporated in their entirety by reference.

What is claimed is:
1. A process for preparing (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one I, having the structure:

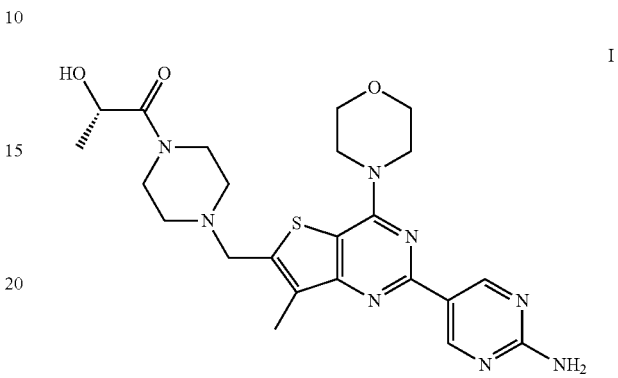

and stereoisomers, geometric isomers, tautomers, and pharmaceutically acceptable salts thereof, comprising:
(a) reacting a salt of (S)-2-hydroxy-1-(piperazin-1-yl)propan-1-one 6 and 2-chloro-7-methyl-4-morpholinothieno[3,2-d]pyrimidine-6-carbaldehyde IV with a reducing agent to give (S)-1-(4-((2-chloro-7-methyl-4-morpholinothieno[3,2-d]pyrimidin-6-yl)methyl)piperazin-1-yl)-2-hydroxypropan-1-one II

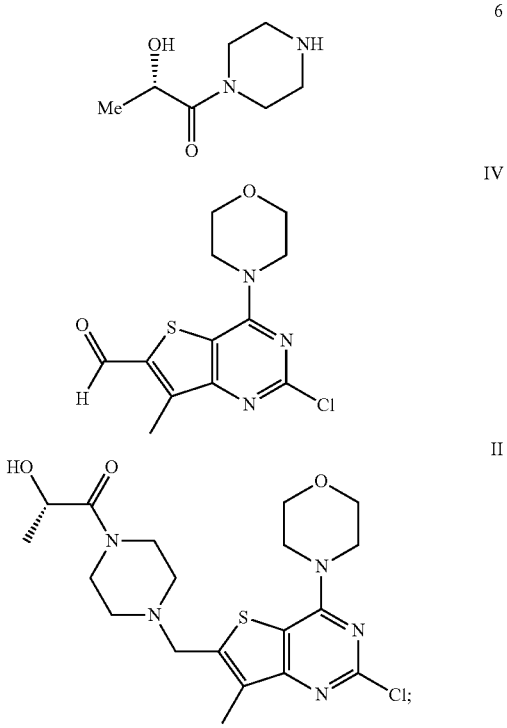

and
(b) reacting II, a palladium catalyst, and 2-aminopyrimidin-5-ylboronic acid III having the structure:

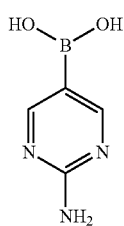

to give I.

2. The process of claim 1 wherein the salt of (S)-2-hydroxy-1-(piperazin-1-yl)propan-1-one 6 is the oxalate salt.

3. The process of claim 2 wherein the oxalate salt of (S)-2-hydroxy-1-(piperazin-1-yl)propan-1-one is prepared by a process comprising reacting (S)-ethyl2-hydroxypropanoate with piperazine, followed by oxalic acid.

4. The process of claim 2 wherein the oxalate salt (S)-2-hydroxy-1-(piperazin-1-yl)propan-1-one V having the structure:

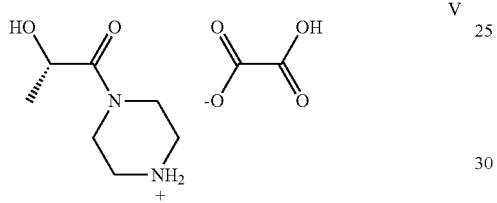

is prepared by a process comprising:
(a) reacting (S)-ethyl 2-hydroxypropanoate 7 with 1-benzylpiperazine to give (S)-1-(4-benzylpiperazin-1-yl)-2-hydroxypropan-1-one 8 having the structure:

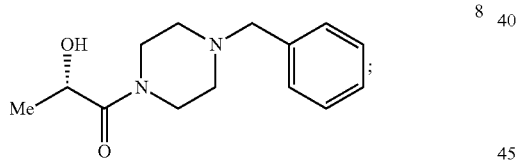

(b) reducing 8 with a palladium catalyst to give (S)-2-hydroxy-1-(piperazin-1-yl)propan-1-one 6 having the structure:

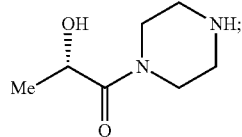

and
(c) reacting (S)-2-hydroxy-1-(piperazin-1-yl)propan-1-one with oxalic acid to give V.

5. The process of claim 2 wherein the oxalate salt (S)-2-hydroxy-1-(piperazin-1-yl)propan-1-one V is prepared by a process comprising:
(a) acetylation of (S)-2-hydroxypropanoic acid (L-lactic acid) 1 to give (S)-2-acetoxypropanoic acid;

(b) reacting (S)-2-acetoxypropanoic acid with a chlorinating reagent to give (S)-1-chloro-1-oxopropan-2-yl acetate;

(c) reacting S)-1-chloro-1-oxopropan-2-yl acetate with 1-benzylpiperazine to give (S)-1-(4-benzylpiperazin-1-yl)-1-oxopropan-2-yl acetate;

(d) hydrolysis of the acetate of (S)-1-(4-benzylpiperazin-1-yl)-1-oxopropan-2-yl acetate to give (S)-1-(4-benzylpiperazin-1-yl)-2-hydroxypropan-1-one;

(e) reductive removal of the benzyl group of (S)-1-(4-benzylpiperazin-1-yl)-2-hydroxypropan-1-one with a palladium catalyst to give (5)-2-hydroxy-1-(piperazin-1-yl)propan--one; and (f) reacting (S)-2-hydroxy-1-(piperazin-1-yl)propan-1-one with oxalic acid to give V.

6. The process of claim 1 wherein 2-aminopyrimidin-5-ylboronic acid III is prepared by a process comprising:

(a) reacting 5-bromopyrimidin-2-amine with a Boc protecting reagent to give bis-tert-butyl 5-bromopyrimidin-2-yl-dicarbamate 10 having the structure:

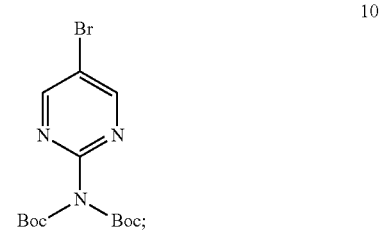 [SMILES: CC(C)(C)OC(=O)N(C(=O)OC(C)(C)C)c1ncc(Br)cn1]

(b) basic hydrolysis of one Boc group to give tert-butyl 5-bromopyrimidin-2-ylcarbamate 11 having the structure:

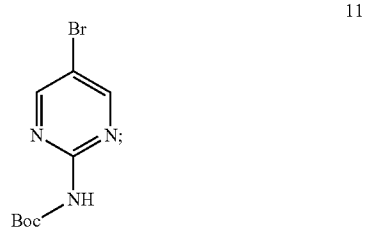

(c) metallation of 11 with an alkyl lithium reagent and borylation with a trialkyl borate reagent to give 2-(tert-butoxycarbonylamino)pyrimidin-5-ylboronic acid 12; and (d) acidic deprotection of the Boc group of 12 to give III.

7. The process of claim 1 wherein 2-aminopyrimidin-5-ylboronic acid III is prepared by a process comprising:

(a) reacting 5-bromopyrimidin-2-amine with lithium bis(trimethylsilyl)amide and then n-butyllithium, followed by a trialkyl borate reagent; and (b) treatment of the mixture with aqueous acid to give III.

8. The process of claim 1 wherein 2-chloro-7-methyl-4-morpholinothieno[3,2-d]pyrimidine-6-carbaldehyde IV is prepared by a process comprising reacting 4-(2-chloro-7-methylthieno[3,2-d]pyrimidin-4-yl)morpholino VI having the structure:

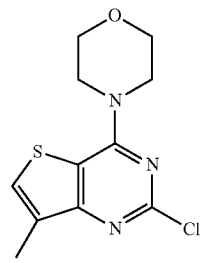

with a Grignard reagent, an alkyl lithium reagent, and dimethylformamide.

9. The process of claim 1 wherein 2-aminopyrimidin-5-ylboronic acid III is prepared by a process comprising:
(a) reacting 4,4,4',4',5,5,5',5'-octamethyl-2,2'-bi(1,3,2-dioxaborolane and bis-tert-butyl 5-bromopyrimidin-2-yldicarbamate 10 having the structure:

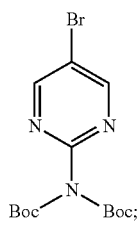

under Buchwald palladium catalysis conditions to give bis-tert-butyl 5-(4,4,5,5-tetramethyl-1,3,2-dioxaborolan-2-yl)pyrimidin-2-yldicarbamate having the structure:

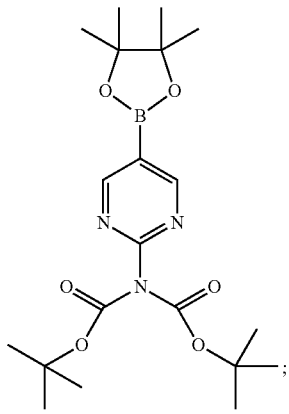 [SMILES: CC(C)(C)OC(=O)N(C(=O)OC(C)(C)C)c1ncc(B2OC(C)(C)C(C)(C)O2)cn1]

and
(b) acidic hydrolysis of both Boc groups and the pinacol group to give III.

10. The process of claim 8 wherein 4-(2-chloro-7-methylthieno[3,2-d]pyrimidin-4-yl)morpholino VI is prepared by a process comprising reacting 2,4-dichloro-7-methylthieno[3,2-d]pyrimidine VII having the structure:

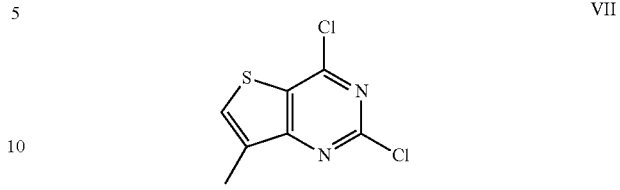

with morpholine.

11. The process of claim 10 wherein 2,4-dichloro-7-methylthieno[3,2-d]pyrimidine VII is prepared by a process comprising reacting 7-methylthieno[3,2-d]pyrimidine-2,4(1H,3H)-dione VIII having the structure:

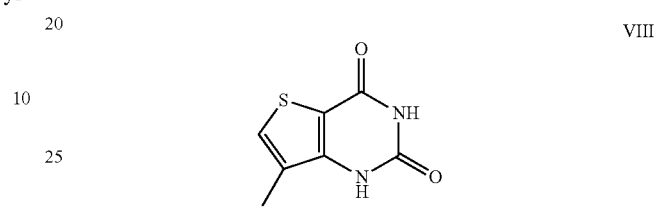

with phosphorus oxychloride.

12. The process of claim 11 wherein 7-methylthieno[3,2-d]pyrimidine-2,4(1H,3H)-dione VIII is prepared by a process comprising reacting methyl 3-amino-4-methylthiophene-2-carboxylate IX having the structure:

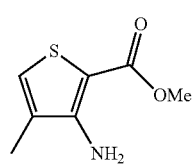

with potassium cyanate.

13. The process of claim 1 wherein the palladium catalyst is selected from $PdCl_2(PPh_3)_2$, $Pd(t-Bu)_3$, $PdCl_2$ dppf $CH_2Cl_2$, $Pd(PPh_3)_4$, $Pd(OAc)/PPh_3$, $Cl_2Pd[(Pet_3)]_2$, $Pd(DIPHOS)_2$, $Cl_2Pd(Bipy)$, $[PdCl(Ph_2PCH_2PPh_2)]_2$, $Cl_2Pd[P(o-tol)_3]_2$, $Pd_2(dba)_3/P(o-tol)_3$, $Pd_2(dba)/P(furyl)_3$, $Cl_2Pd[P(furyl)_3]_2$, $Cl_2Pd(PMePh_2)_2$, $Cl_2Pd[P(4-F-Ph)_3]_2$, $Cl_2Pd[P(C_6F_6)_3]_2$, $Cl_2Pd[P(2-COOH-Ph)(Ph)_2]_2$, and $Cl_2Pd[P(4-COOH-Ph)(Ph)_2]_2$.

14. The process of claim 1 wherein the reducing agent is sodium triacetoxyborohydride, 2-picoline borane, or 5-ethyl-2-methylpyridine borane.

15. The process of claim 1 further comprising filtering the reaction mixture through activated carbon after reacting II, the palladium catalyst, and 2-aminopyrimidin-5-ylboronic acid III.

* * * * *